United States Patent
Nakashiro et al.

(10) Patent No.: US 8,716,175 B2
(45) Date of Patent: May 6, 2014

(54) CATALYST FOR PRODUCING ETHYLENE OXIDE, PROCESS FOR PRODUCING THE CATALYST AND PROCESS FOR PRODUCING ETHYLENE OXIDE

(75) Inventors: Katsumi Nakashiro, Yokkaichi (JP); Soichiro Yamada, Yokkaichi (JP); Takanao Matsumoto, Yokkaichi (JP)

(73) Assignee: Mitsubishi Chemical Corporation, Tokyo (JP)

( * ) Notice: Subject to any disclaimer, the term of this patent is extended or adjusted under 35 U.S.C. 154(b) by 750 days.

(21) Appl. No.: 12/083,876

(22) PCT Filed: Mar. 30, 2007

(86) PCT No.: PCT/JP2007/000352
§ 371 (c)(1),
(2), (4) Date: Mar. 17, 2009

(87) PCT Pub. No.: WO2007/116585
PCT Pub. Date: Oct. 18, 2007

(65) Prior Publication Data
US 2009/0192324 A1    Jul. 30, 2009

(30) Foreign Application Priority Data

Apr. 10, 2006  (JP) ................................ 2006-107329
Apr. 10, 2006  (JP) ................................ 2006-107330

(51) Int. Cl.
*B01J 23/48*    (2006.01)

(52) U.S. Cl.
USPC ............ 502/347; 502/241; 502/344; 502/348

(58) Field of Classification Search
USPC .......................... 502/241, 317, 344, 347–348
See application file for complete search history.

(56) References Cited

U.S. PATENT DOCUMENTS

| | | |
|---|---|---|
| 4,761,394 A | 8/1988 | Lauritzen |
| 4,766,105 A | 8/1988 | Lauritzen |
| 4,808,738 A | 2/1989 | Lauritzen |
| 4,812,437 A | 3/1989 | Nojiri et al. |
| 4,820,675 A | 4/1989 | Lauritzen |
| 4,833,261 A | 5/1989 | Lauritzen |
| 4,939,114 A | 7/1990 | Nojiri et al. |
| 5,187,140 A | 2/1993 | Thorsteinson et al. |
| 5,705,661 A | 1/1998 | Iwakura et al. |
| 6,368,998 B1 | 4/2002 | Lockemeyer |
| 7,485,597 B2 | 2/2009 | Lockemeyer et al. |
| 2004/0049061 A1 | 3/2004 | Lockemeyer et al. |

FOREIGN PATENT DOCUMENTS

| | | |
|---|---|---|
| EP | 0 247 414 A2 | 12/1987 |
| EP | 0 266 015 A1 | 5/1988 |
| EP | 0 315 911 A1 | 5/1989 |
| EP | 0 425 020 A1 | 5/1991 |
| EP | 0 716 884 A2 | 6/1996 |
| EP | 0 716 884 A3 | 11/1996 |
| EP | 0764464 A2 | 3/1997 |
| JP | 63-116743 | 5/1988 |
| JP | 63-126552 | 5/1988 |
| JP | 01-123629 | 5/1989 |
| JP | 03-207447 | 9/1991 |
| JP | 09-150058 | 6/1997 |
| JP | 2002-248351 | 9/2002 |
| JP | 2006-021199 | 1/2006 |
| WO | WO 00/15333 | 3/2000 |
| WO | WO 00/15333 A1 | 3/2000 |
| WO | WO 2004/002954 A2 | 1/2004 |
| WO | WO 2004002954 A2 * | 1/2004 |
| WO | WO 2004/101144 A1 | 11/2004 |
| WO | 2005/097318 | 10/2005 |
| WO | WO 2006/002718 A1 | 1/2006 |

OTHER PUBLICATIONS

Thompson, Acid, based, pH/pKa calculations and the Henderson Hasselbalch equation, 2004, pp. 1-14.*
Notice of Reasons for Rejection and English translation in JP 2007-093485 mailed May 31, 2011.
Notice of Reasons for Rejection and English translation in JP 2007-093485 mailed Nov. 15, 2011.
English translation of Chinese Office Action in SN 201010527073.8 issued Apr. 26, 2012.
English translation of Chinese Office Action in SN 201010527074.2 issued Apr. 27, 2012.
Supplementary European Search Report in EP 07 73 7009 dated Jan. 16, 2013.
English translation of Notice of Reasons for Rejection in JP 2007-093485 issued Jan. 8, 2013.
English translation of Notice of Rejection in JP 2007-93058 issued May 31, 2011.
Official Action in EP 13 18 4300 dated Dec. 5, 2013.
Supplementary European Search Report in EP 13 18 4299 dated Nov. 28, 2013.
International Search Report for PCT/JP2007/000352 mailed Jun. 19, 2007.
English translation of Chinese Action in Serial No. 200780001737.3 dated Jun. 10, 2010.

* cited by examiner

*Primary Examiner* — Kaj K Olsen
*Assistant Examiner* — Pritesh Darji
(74) *Attorney, Agent, or Firm* — Nixon & Vanderhye P.C.

(57) ABSTRACT

There is provided a catalyst for producing ethylene oxide from ethylene which is composed of at least silver (Ag), cesium (Cs), rhenium (Re) and a carrier, and can be improved, in particular, in selectivity.

The present invention relates to a catalyst for producing ethylene oxide from ethylene, comprising at least silver (Ag), cesium (Cs), rhenium (Re) and a carrier, said catalyst being produced by optionally pretreating the carrier to support an alkali metal thereon and then supporting Ag, Cs and Re on the carrier, wherein the carrier has a specific surface area of 0.6 to 3.0 $m^2/g$ and a weight ratio of a silicon (Si) content to a sodium (Na) content of 2 to 50 in terms of $SiO_2/Na_2O$; a content of Re in the catalyst is 170 to 600 ppm per 1 $m^2/g$ of the specific surface area of the carrier on the basis of a weight of the carrier; and a molar ratio of Cs to Re in the catalyst is 0.3 to 19.

6 Claims, No Drawings

US 8,716,175 B2

CATALYST FOR PRODUCING ETHYLENE OXIDE, PROCESS FOR PRODUCING THE CATALYST AND PROCESS FOR PRODUCING ETHYLENE OXIDE

This application is the U.S. national phase of International Application No. PCT/JP2007/000352 filed 30 Mar. 2007 which designated the U.S. and claims priority to Japanese Patent Applications No. 2006-107329 filed 10 Apr. 2006 and 2006-107330 filed 10 Apr. 2006, the entire contents of each of which are hereby incorporated by reference.

FIELD OF THE INVENTION

The present invention relates to a catalyst for producing ethylene oxide, a process for producing the catalyst, and a process for producing ethylene oxide.

RELATED ARTS

Catalysts used for producing ethylene oxide from ethylene contain silver (Ag) as a main component which is supported on a carrier. In the catalysts used in industrial processes, elements such as alkali metals and rhenium (Re) acting as a co-catalyst are added to Ag as a main component thereof in order to enhance the catalyst performance (Japanese Patent Application Laid-open (KOKAI) No. 9-150058 (1997)).

As to the effects of the alkali metals, it has been conventionally reported that the alkali metals exhibit the effect of neutralizing acid sites on the carrier when existing on the carrier, the effect of modifying a catalytic activity of Ag when existing on the surface of Ag, etc. However, details of these effects of the alkali metals conventionally reported are still unclear. On the other hand, it has also been reported that rhenium (Re) is essentially required to coexist with the alkali metals in order to allow the rhenium to suitably act as a co-catalyst, although sites of Re in the catalyst as well as its effects and mechanism upon acting as a co-catalyst are not clearly known (Japanese Patent Application Laid-open (KOKAI) No. 63-126552 (1988)).

The carrier used in the above catalysts is usually constituted of α-alumina as a main component. The α-alumina carrier has been produced by calcining a mixture of a raw α-alumina powder, a binder and a pore-forming agent. The thus produced carrier usually contains impurities such as silicon (Si) and sodium (Na). The Si content in the carrier is from 0.1 to several tens percents by weight in terms of $SiO_2$, whereas the Na content in the carrier is from 0.01 to several percents by weight in terms of $Na_2O$.

It has been reported that the amount of Si and/or Na contained in the carrier tends to have a significant influence on a performance of the catalysts comprising Ag, the alkali metal and the carrier containing no Re as a co-catalyst (Japanese Patent Application Laid-open (KOKAI) Nos. 63-116743 (1988) and 1-123629 (1989)). Therefore, it has been required to control the amount of Si and/or Na contained in the raw α-alumina powder, binder and pore-forming agent as well as in the carrier. In addition, there has been reported the Re-containing catalyst whose Ag content is controlled to not less than 20% by weight (Japanese Patent Application Laid-open (KOKAI) No. 3-207447 (1991) and WO 2005-097318).

DISCLOSURE OF THE INVENTION

Problem to be Solved by the Invention

As a result of the present inventors' earnest study for the purpose of providing an improved catalyst for producing ethylene oxide which comprises at least Ag, Cs, Re and a carrier, or at least Ag, Li, Cs, Re and a carrier, there have been found the following findings (1) and (2):

(1) In the conventional catalysts comprising a carrier having a large surface area, Ag, Cs and Re, it was considered that the Si or Na component contained in the carrier usually had no influence on properties of Re as a co-catalyst. However, when a ratio between the Si and Na components contained in the carrier is adjusted to a specific range, the resultant catalyst can be unexpectedly enhanced in a co-catalyst effect of Re and considerably improved in selectivity.

(2) When using a carrier having a large specific surface area and increasing a Li content in the catalyst, the obtained catalyst can be unexpectedly considerably improved in catalyst life while maintaining a high selectivity.

Means for Solving the Problem

The present invention has been made on the basis of the above findings. The present invention provides a series of the following aspects associated with each other.

The first aspect of the present invention is based on the above finding (1). That is, in the first aspect of the present invention, there is provided a catalyst for producing ethylene oxide from ethylene, comprising at least silver (Ag), cesium (Cs), rhenium (Re) and a carrier, which catalyst is produced by optionally pretreating the carrier to support an alkali metal thereon and then supporting Ag, Cs and Re on the carrier, in which the carrier has a specific surface area of 0.6 to 3.0 $m^2/g$ and a weight ratio of a silicon (Si) content to a sodium (Na) content of 2 to 50 in terms of $SiO_2/Na_2O$; a content of Re in the catalyst is 170 to 600 ppm per 1 $m^2/g$ of the specific surface area of the carrier on the basis of a weight of the carrier; and a molar ratio of Cs to Re (Cs/Re) in the catalyst is 0.3 to 19.

The second aspect of the present invention has been attained as a result of the further present inventors' study based on the above finding (1). In the second aspect of the present invention, there is provided a catalyst for producing ethylene oxide from ethylene, comprising at least silver (Ag), cesium (Cs), rhenium (Re) and a carrier, which catalyst is produced by optionally pretreating the carrier to support an alkali metal thereon and then supporting Ag, Cs and Re on the carrier, in which the carrier has a specific surface area of 0.6 to 3.0 $m^2/g$ and contains acid sites having a pKa value of not more than 5.0; a content of Re in the catalyst is 170 to 600 ppm per 1 $m^2/g$ of the specific surface area of the carrier on the basis of a weight of the carrier; and a molar ratio of Cs to Re in the catalyst is 0.3 to 19.

In the other aspect of the present invention, there is provided a process for producing the catalyst as defined in the above first aspect of the present invention which comprises at least silver (Ag), cesium (Cs), rhenium (Re) and a carrier, in which a procedure for supporting Ag on the carrier is conducted by two or more divided operations, and at least a part of an amount of each of Cs and Re to be contained in the catalyst is supported on the carrier simultaneously with the final operation of the procedure for supporting Ag on the carrier.

In the still other aspect of the present invention, there is provided a process for producing the catalyst as defined in the above second aspect of the present invention which comprises at least silver (Ag), cesium (Cs), rhenium (Re) and a carrier, in which a procedure for supporting Ag on the carrier is conducted by two or more divided operations, and at least a part of an amount of each of Cs and Re to be contained in the catalyst is supported on the carrier simultaneously with the final operation of the procedure for supporting Ag on the carrier.

In the still other aspect of the present invention, there is provided a process for producing ethylene oxide, comprising the step of oxidizing ethylene in the presence of the catalyst as defined in the above first aspect of the present invention.

In the still other aspect of the present invention, there is provided a process for producing ethylene oxide, comprising the step of oxidizing ethylene in the presence of the catalyst as defined in the above second aspect of the present invention.

The third aspect of the present invention is based on the above finding (2). In the third aspect of the present invention, there is provided a catalyst for producing ethylene oxide from ethylene, comprising at least silver (Ag), lithium (Li), cesium (Cs), rhenium (Re) and a carrier, in which as the carrier, a carrier having a specific surface area of 0.6 to 3.0 m$^2$/g is used; and a content of Li in the catalyst is 400 to 1000 ppm on the basis of a weight of the carrier.

In the other aspect of the present invention, there is provided a process for producing the catalyst as defined in the above third aspect of the present invention which comprises at least silver (Ag), lithium (Li), cesium (Cs), rhenium (Re) and a carrier, in which a procedure for supporting Ag on the carrier is conducted by two or more divided operations, and at least a part of an amount of each of Cs and Re to be contained in the catalyst is supported on the carrier simultaneously with the final operation of the procedure for supporting Ag on the carrier.

In the still other aspect of the present invention, there is provided a process for producing ethylene oxide, comprising the step of oxidizing ethylene in the presence of the catalyst as defined in the above third aspect of the present invention.

Effect of the Invention

In accordance with the first and second aspects of the present invention, there is provided a catalyst for producing ethylene oxide, which comprises at least Ag, Cs, Re and a carrier and can be improved, in particular, in selectivity. Also, in accordance with the third aspect of the present invention, there is provided a catalyst for producing ethylene oxide, which comprises at least Ag, Li, Cs, Re and a carrier and can be improved, in particular, in catalyst life.

PREFERRED EMBODIMENTS FOR CARRYING OUT THE INVENTION

The present invention is described in detail hereinunder.
<Catalyst According to the First Aspect of the Present Invention>

The catalyst according to the first aspect of the present invention comprises at least Ag, Cs, Re and a carrier. In the preferred embodiment of the first aspect of the present invention, the catalyst further contains Li.

As the carrier, there may be used a porous refractory material such as alumina, silicon carbide, titania, zirconia and magnesia. Among these materials, especially preferred are porous refractory materials containing α-alumina as a main component. These porous refractory materials may be produced by calcining a mixture of a raw powder, a binder and a pore-forming agent, and contain impurities such as a Si component and a Na component. The Si content in the carrier is usually 0.5 to 7.0% by weight and preferably 1.8 to 7.0% by weight in terms of $SiO_2$, whereas the Na content in the carrier is usually 0.05 to 0.50% by weight and preferably 0.16 to 0.45% by weight in terms of $Na_2O$. The ranges of the Si and Na contents are values determined from the standpoint of enhancing a selectivity of the resultant catalyst.

In the first aspect of the present invention, there is used such a carrier having a large surface area and a ratio between the Si and Na components which lies within a specific range. More specifically, the carrier used in the first aspect of the present invention has a specific surface area of 0.6 to 3.0 m$^2$/g, and a weight ratio of the Si content to the Na content therein lies within the range of 2 to 50 in terms of $SiO_2/Na_2O$. When the carrier satisfies the above requirements, the co-catalyst effect of Re can be enhanced, so that the resultant catalyst can be considerably improved in selectivity.

The specific surface area of the carrier is preferably 0.8 to 2.0 m$^2$/g and more preferably 1.2 to 1.6 m$^2$/g from the standpoint of a good catalyst life, in particular, for keeping a high selectivity of the catalyst. The weight ratio of the Si content to the Na content in the carrier is preferably 6 to 27, in particular, from the standpoint of improving a selectivity of the catalyst. Meanwhile, the above specific surface area is the value measured by B.E.T. method.

The porous refractory materials for the catalyst carrier, in particular, α-alumina, are commercially available with various grades which are different in specific surface area or contents of impurities from each other. Therefore, the carrier used in the first aspect of the present invention may be adequately selected from the commercially available porous refractory materials capable of satisfying the above properties. Also, the contents of the Si and Na components in the carrier may be controlled by washing the carrier with an acid aqueous solution having an adequate concentration.

The content of silver in the catalyst is usually 5 to 40% by weight on the basis of a whole weight of the catalyst, and preferably 15 to 30% by weight from the standpoint of a good effect of improving the catalyst life. The content of Cs in the catalyst is usually 10 to 10000 ppm and preferably 50 to 5000 ppm similarly to the conventionally known catalysts.

The Cs content is determined depending upon the below-mentioned Re content, and it is required to control the Cs content such that a molar ratio of Cs to Re (Cs/Re) in the catalyst lies within the range of 0.3 to 19. The molar ratio of Cs to Re is preferably 1.7 to 4.5 and more preferably 2.2 to 4.5. When the molar ratio of Cs to Re is less than 0.3 or more than 19, the effect of improving a selectivity of the catalyst tends to be insufficient.

The Re content is determined depending upon the specific surface area of the carrier used, and is usually 170 to 600 ppm, preferably 200 to 500 ppm and more preferably 250 to 450 ppm per 1 m$^2$/g of the specific surface area of the carrier (before being incorporated into the catalyst). When the Re content is less than 170 ppm/(m$^2$/g) or more than 600 ppm/(m$^2$/g), the effect of improving a selectivity of the catalyst tends to be insufficient.

In the first aspect of the present invention, the carrier may be optionally pretreated to support an alkali metal thereon. Such a pretreatment of the carrier is recommended from the standpoint of further enhancing the catalyst performance. The "pretreatment" used herein means the treatment for supporting an alkali metal on the carrier before supporting a silver compound thereon. As the alkali used in the pretreatment, there may be usually used Li and/or Cs and preferably both of Li and Cs. Meanwhile, Cs in the above molar ratio (Cs/Re) means the content of Cs supported on the catalyst in the post-treatment (treatment for supporting Ag, Re and Cs thereon). It is considered that Cs supported on the catalyst in the post-treatment is present together with Re on the surface of Ag.

The amounts of Li and Cs used in the pretreatment are controlled such that the Li or Cs content in the carrier after the pretreatment is usually 100 to 1000 ppm. The Li content is preferably 400 to 1000 ppm, more preferably 550 to 1000 ppm and still more preferably 585 to 1000 ppm, whereas the Cs content is preferably 100 to 500 ppm. When the Li or Cs content in the carrier is less than 100 ppm, the effect of improving the catalyst life tends to be insufficient. When the Li or Cs content in the carrier is more than 1000 ppm, the above effect tends to be already saturated, resulting in uneconomical procedure. Meanwhile, Cs used in the pretreatment is different from Cs used in the post-treatment in that the former is directly supported on the carrier. This is because it is suggested that Cs used in the post-treatment is caused to adhere onto Ag together with Re.

In the catalyst for producing ethylene oxide according to the first aspect of the present invention, from the standpoint of a good effect of improving the catalyst life, the molar ratio of Li to Re (Li/Re) is usually 6 to 63, preferably 25 to 63, more preferably 35 to 63 and still more preferably 37 to 63, and the weight ratio of Li to Ag (Li/Ag) is usually 0.0007 to 0.0073, preferably 0.0029 to 0.0073, more preferably 0.004 to 0.0073 and still more preferably 0.0043 to 0.0073.

In the above pretreatment, the alkali metals (Li and Cs) may be supported on the carrier using a water-soluble alkali metal compound according to conventionally known methods. Examples of the alkali metal compound may include nitrates, hydroxides, halides, carbonates, bicarbonates, oxalates, carboxylates, etc., of alkali metals. Among these alkali metal compounds, preferred are carbonates of alkali metals. These alkali metal compounds may be used in the form of an aqueous solution having an adequate concentration depending upon the contents of the respective alkali metals in the carrier.

In the above post-treatment, there may be suitably used a catalyst-impregnating solution prepared by dissolving a water-soluble Re compound and a water-soluble Cs compound, if required, together with a water-soluble Li compound in a Ag-amine complex solution.

Examples of the Ag compound used in the Ag-amine complex solution may include silver oxide, silver nitrate, silver carbonate, silver acetate and silver oxalate. Examples of the amine used in the Ag-amine complex solution may include monoamines such as ammonia, pyridine and butylamine, alkanol amines such as ethanolamine, and polyamines such as ethylenediamine and 1,3-diaminopropane. Examples of the water-soluble Re compound may include rhenium halides, rhenium oxyhalides, salts of rhenic acid and salts of perrhenic acid. Examples of the Cs compound may include those compounds as used in the pretreatment. Among these Cs compounds, preferred are nitrates and hydroxides of Cs. The concentrations of the respective components in the catalyst-impregnating solution may be appropriately determined depending upon the contents of the respective components in the catalyst.

As the impregnating method in the above pretreatment, there may be used the method of immersing the carrier in the solution, the method of spraying the solution over the carrier, etc. As the drying treatment, there may be used the method of separating the carrier and an excess amount of the solution from each other after the impregnating treatment, and then drying the thus separated carrier either under reduced pressure or under heating. The heat treatment may be conducted by using air or an inert gas such as nitrogen, or superheated steam. The heating temperature is usually 100 to 300° C. and preferably 130 to 270° C.

As the impregnating treatment in the post-treatment, there may be used the same methods as used in the pretreatment. The heat treatment after the impregnating treatment may be conducted by keeping the temperature and time required for supporting Ag metal on the carrier. The conditions for the heat treatment are preferably determined such that Ag-amine complex is reduced into the metal in the form of as uniform and fine particles as possible on the carrier. The heat treatment may be performed by using heated air (or an inert gas such as nitrogen) or superheated steam. The heating temperature is usually 130 to 300° C., and the heating time is usually 5 to 30 min.

In particular, the catalyst having a high Ag-supporting rate, for example, an Ag-supporting rate of 15 to 30% by weight (on the basis of a weight of the catalyst) may be readily produced by the process for producing the catalyst according to the present invention, more specifically, the process wherein a procedure for supporting Ag on the carrier is conducted by two or more divided operations, and at least a part of an amount of each of Cs and Re to be contained in the catalyst is supported on the carrier simultaneously with the final operation of the procedure for supporting Ag on the carrier. From the standpoint of a good catalyst performance, more than half an amount of each of Cs and Re to be contained in the catalyst is preferably supported on the carrier simultaneously with the final operation of the Ag-supporting procedure. The amount of each of Cs and Re which is to be supported on the carrier simultaneously with the final operation of the Ag-supporting procedure is more preferably not less than ¾ of the amount of each of Cs and Re and most preferably a whole amount of each of Cs and Re. Also, the components other than Cs and Re may be supported in the same manner as described above. Thus, in the process for producing the catalyst according to the present invention, at least a part of the respective components such as Cs and Re is supported on the carrier simultaneously with the final operation of the Ag-supporting procedure. If Cs, Re, etc., are separately supported on the carrier after the final operation of the Ag-supporting procedure, the resultant catalyst tends to be deteriorated in catalyst performance.

The process for producing ethylene oxide using the catalyst according to the first aspect of the present invention may be performed under known conditions. The reaction pressure is usually 0 to 3.5 MPaG, and the reaction temperature is usually 180 to 350° C. and preferably 200 to 300° C. As the reaction raw material gas, there may be generally used a mixed gas comprising 1 to 40% by volume of ethylene and 1 to 20% by volume of molecular oxygen. Further, in general, a diluent, e.g., an inert gas such as methane and nitrogen may be present in the reaction system at a suitable mixing ratio (e.g., in an amount of 1 to 70% by volume). As the molecular oxygen-containing gas, there may be usually used air or industrial oxygen. In addition, the reaction raw material gas may also contain a reaction modifier such as, for example, halogenated hydrocarbons, in an amount of about 0.1 to 50 ppm in order to prevent hot spots from being formed in the catalyst, and considerably improve the catalyst performance, in particular, selectivity.

<Catalyst According to the Second Aspect of the Present Invention>

The catalyst according to the second aspect of the present invention is used for producing ethylene oxide from ethylene, and comprises at least silver (Ag), cesium (Cs), rhenium (Re) and a carrier. The catalyst according to the second aspect of the present invention is produced by optionally pretreating the carrier to support an alkali metal thereon and then supporting Ag, Cs and Re on the carrier. The above carrier has a specific surface area of 0.6 to 3.0 m²/g and contains acid sites having a pKa value of not more than 5.0. The content of Re in the catalyst is 170 to 600 ppm per 1 m²/g of the specific surface area of the carrier on the basis of a weight of the carrier, and a molar ratio of Cs to Re (Cs/Re) in the catalyst is 0.3 to 19. More specifically, the second aspect of the present invention is different from the first aspect of the present invention in that the acid sites present on the carrier is defined instead of the ratio of $SiO_2/Na_2O$ defined in the first aspect of the present invention. By defining such acid sites, the co-catalyst effect of Re can be enhanced similarly to the definition of the ratio of $SiO_2/Na_2O$.

The acid sites defined in the second aspect of the present invention have an appropriate intensity represented by a pKa value of not more than 5.0, and such acid sites can be determined by color reaction using methyl red as an indicator. The acid sites having an intensity represented by a pKa value of not more than 3.2 have no adverse influence on a selectivity of the catalyst as long as the amount of the acid sites is small to such an extent exhibiting merely a weak color reaction. However, when the amount of the acid sites is increased to such an extent exhibiting a strong color reaction, the resultant catalyst tends to be undesirably deteriorated in selectivity. The acid sites represented by a pKa value of not more than 3.2 are determined by color reaction using methyl yellow as an indicator. On the other hand, the base sites represented by a pKa value of not less than 7.3 is also undesirable. The base sites represented by a pKa value of not less than 7.3 are determined by color reaction using bromothymol blue as an indicator.

The acidity and basicity on the surface of the carrier can be readily determined by color reaction using an indicator (TANABE, Kozo and TAKESHITA, tsuneichi "Acid and Base Catalysts" published by Sangyo Tosho Co., Ltd., Apr. 26, 1966, p. 161; "Separate Volume for Lecture on Catalysts; Handbook for Catalyst Experiments" published by Kodansha Ltd. and edited by Catalysis Society of Japan, p. 170; and "Handbook of Chemistry, Fundamental Volume; the 3rd Edition" published by Maruzen Co., Ltd., and edited by the Chemical Society of Japan, Jun. 25, 1984, p. II-342).

Also, the amount of the acid sites in the carrier may be determined by subjecting a sample colored with the above indicator to titration using a base such as n-butylamine. The color reaction using the above indicator and the terminal points of the titration using the base may be usually sufficiently determined by visual observation.

<Catalyst According to the Third Aspect of the Present Invention>

The catalyst for producing ethylene oxide according to the third aspect of the present invention comprises at least Ag, Li, Cs, Re and a carrier similarly to the catalyst according to the preferred embodiment of the first aspect of the present invention.

In the third aspect of the present invention, there is used the carrier having a specific surface area of 0.6 to 3.0 m²/g similarly to the carrier used in the catalyst according to the first aspect of the present invention. However, in the third aspect of the present invention, the ratio of the Si component to the Na component ($SiO_2/Na_2O$) as defined in the first aspect of the present invention is not an essentially required condition but merely a preferred condition. The other conditions for the carrier are the same as those described in the first aspect of the present invention.

In the third aspect of the present invention, the content of Li in the catalyst is 400 to 1000 ppm on the basis of the weight of the carrier. The Li content in the catalyst according to the third aspect of the present invention is identical to the preferred range as described in the first aspect of the present invention. Also, in the third aspect of the present invention, the contents of Cs and Re and the molar ratio of Cs to Re (Cs/Re) as defined in the first aspect of the present invention are not essentially required conditions but merely preferred conditions. The other conditions for the catalyst components are the same as described in the first aspect of the present invention. Further, the production process and the use method concerning the catalyst according to the third aspect of the present invention are also the same as those described in the first aspect of the present invention.

EXAMPLES

The present invention is described in more detail by the following examples. However, these examples are only illustrative and not intended to limit the scope of the present invention. Meanwhile, in the following Examples and Comparative Examples, various properties were measured by the following methods. Also, the symbol "A" suffixed to the respective Example Nos. and Comparative Example Nos. means that those Examples and Comparative Examples relate to the first aspect of the present invention, whereas the symbol "B" suffixed to the respective Example Nos. and Comparative Example Nos. means that those Examples and Comparative Examples relate to the second aspect of the present invention.

(1) Specific Surface Area:

The specific surface area was measured by B.E.T. method. The nitrogen absorption was conducted at a temperature of 77 K, and the specific surface area was calculated by BET 1-point method.

(2) Contents of Si and Na in Carrier:

A sample was pulverized and then pressure-molded, and contents of Si and Na in the obtained molded product were measured by a fluorescent X-ray analysis.

(3) Contents of Cs, Re and Li in Pretreated Carrier and Catalyst:

The respective components were extracted with nitric acid, and the contents of Cs and Li were measured by an atomic absorption method, whereas the content of Re was measured by an ICP emission spectrum method.

(4) Content of Ag in Catalyst:

Ag was extracted with nitric acid, and the Ag content was measured by a potentiometric titration method.

(5) Acidity and Basicity of Carrier:

The acidity or basicity of the carrier was measured by the following method. That is, the carrier was dried at 120° C. for 3 hr, cooled and then charged into dried toluene. Several droplets of a solution prepared by dissolving respective indicators in toluene (concentration: 0.001% by weight) were added to the carrier immersed in toluene, and the resultant mixture was fully shaken and then allowed to stand to examine occurrence or non-occurrence of a color reaction for each indicator.

Example 1A (1) Measurement of Acidity or Basicity of Carrier

The acidity or basicity of an α-alumina carrier (specific surface area: 1.0 m²/g; water absorption: 35.7% by weight; $SiO_2$ content: 3.0% by weight; $Na_2O$ content: 0.35% by weight; weight ratio $SiO_2/Na_2O$: 9; shape: ring shape having a size of 8 mmφ×8 mm) was measured.

The carrier exhibited no red color reaction when using methyl yellow having a pKa value of not more than 3.2 as an indicator, but exhibited a red color reaction when using methyl red having a pKa value of not more than 5.0 as an indicator. Also, the carrier did not exhibit a blue color reaction when using bromothymol blue having a pKa value of not less than 7.3 as an indicator. From the above results, it was confirmed that the carrier had acid sites represented by a pKa value of more than 3.2 and not more than 5.0 (3.2<pKa≤5.0) and no base sites represented by a pKa value of not less than 7.3 (pKa≥7.3).

(2) Pretreatment of Carrier 100 g of the above α-alumina carrier was immersed in 200 mL of an aqueous solution containing 0.156 g of cesium carbonate ($Cs_2CO_3$) and 1.69 g of lithium carbonate ($Li_2CO_3$). The α-alumina carrier was taken out from the aqueous solution, and an excessive amount of the aqueous solution attached to the carrier was removed therefrom. Next, the carrier was heated by superheated steam at 150° C. for 15 min while flowing the steam at a rate of 2 m/sec, thereby producing the carrier impregnated with Li and Cs. As a result, it was confirmed that the content of Li in the carrier was 500 ppm and the content of Cs in the carrier was 230 ppm. Various properties of the carrier used are shown in Table 1.

(3) Preparation of Silver-Amine Complex Solution

After dissolving 322 g of silver nitrate ($AgNO_3$) and 192 g of potassium oxalate monohydrate ($K_2C_2O_4 \cdot H_2O$) in 1.4 L of water and 1.6 L of water, respectively, the resultant aqueous solutions were gradually mixed with each other while heating in a hot water bath at 60° C., thereby obtaining a white precipitate of silver oxalate ($AgC_2O_4$). The reaction mixture was filtered to separate and recover the precipitate therefrom, and the obtained precipitate was washed with distilled water to obtain hydrous silver oxalate (water content: 23.3% by weight). 375 g of the thus obtained hydrous silver oxalate was gradually added and dissolved in an aqueous solution comprising 103 g of ethylenediamine, 28.1 g of 1,3-diaminopropane and 133 g of water, thereby preparing a silver-amine complex solution.

(4) Production of Ag Catalyst 12.7 g of the thus obtained silver-amine complex solution was mixed with 0.6 mL of an aqueous solution containing 5.54% by weight of cesium nitrate ($CsNO_3$), 0.6 mL of an aqueous solution containing 3.05% by weight of ammonium perrhenate ($NH_4ReO_4$) and 2.1 mL of water to prepare an impregnating solution. The thus prepared impregnating solution was impregnated in 30 g of the α-alumina carrier impregnated with Li and Cs in an evaporator under reduced pressure while heating at 40° C. The resultant impregnated carrier was heated by superheated steam at 200° C. for 15 min while flowing the steam at a rate of 2 m/sec, thereby obtaining a catalyst. As a result, it was confirmed that the contents of Ag, Cs, Re and Li in the thus obtained catalyst were 13.6% (12.0% by weight on the basis of the weight of the catalyst), 980 ppm, 420 ppm and 500 ppm, respectively, by weight on the basis of the weight of the carrier.

(5) Oxidation Reaction of Ethylene

The above-obtained Ag catalyst was pulverized into 6 to 10 mesh size. 3 mL of the pulverized catalyst was charged into a reactor of SUS stainless steel tube having an inner diameter of 7.5 mm, and a reaction gas comprising 30% of ethylene, 8.5% of oxygen, 1.5 ppm of vinyl chloride, 6.0% of carbon dioxide and nitrogen as a balance was flowed through the reactor at a GHSV of 4300 $hr^{-1}$ under a pressure of 0.7 MPaG. The reaction temperature was controlled such that a yield (STY) of ethylene oxide produced per unit volume of the catalyst and unit time was 0.25 kg-EO/h·L-cat. The selectivity to ethylene oxide was increased with the passage of evaluation time and thereafter lowered. The respective catalyst components and the catalyst performance of each catalyst are shown in Tables 3 and 4. Meanwhile, the selectivity to ethylene oxide is represented on the basis of ethylene. Also, the term "Cs*" in "Cs*/Re" in Tables 3 and 4 means a content of Cs supported on the catalyst in the post-treatment. In addition, the "deterioration rate" of the catalyst performance means deterioration of the selectivity per 1000 kg-cumulative ethylene oxide (EO)/L-cat, and is represented by unit of "%/EO 1000".

Examples 2A to 12A and Comparative Examples 1A to 11A

Using the respective carriers having properties as shown in Tables 1 and 2, the same procedure for the pretreatment as defined in Example 1A was conducted except that the amounts of lithium carbonate and cesium carbonate used were changed so as to control the contents of Li and Cs upon the pretreatment to those shown in Tables 3 and 4. Next, the "silver-amine complex solution" having the same composition as that obtained in Example 1A was prepared, and then the same procedure for "production of Ag catalyst" as defined in Example 1A was conducted except that the concentrations of cesium nitrate and ammonium perrhenate were changed, thereby obtaining a catalyst having contents of Cs and Re as shown in Tables 3 and 4. Meanwhile, the contents of Ag in the respective catalysts all were 13.6% by weight on the basis of the weight of the carrier used. Next, the respective catalysts were used to conduct an oxidation reaction of ethylene. The respective catalyst components and the catalyst performance of each catalyst are shown in Tables 3 and 4.

TABLE 1

| | Carrier | | | |
|---|---|---|---|---|
| | Specific surface area: SA ($m^2/g$) | Si content (calculated as $SiO_2$) (wt %) | Na content (calculated as $Na_2O$) (wt %) | $SiO_2/Na_2O$ (weight ratio) |
| Example 1A | 1.0 | 3.0 | 0.35 | 9 |
| Example 2A | 1.0 | 3.1 | 0.26 | 12 |
| Example 3A | 1.0 | 5.9 | 0.23 | 26 |
| Example 4A | 1.4 | 5.5 | 0.38 | 14 |
| Example 5A | 1.4 | 2.7 | 0.38 | 7 |
| Example 6A | 1.4 | 5.8 | 0.25 | 23 |
| Example 7A | 1.4 | 3.7 | 0.27 | 14 |
| Example 8A | 1.4 | 2.8 | 0.25 | 11 |
| Example 9A | 1.4 | 3.7 | 0.27 | 14 |
| Example 10A | 1.4 | 3.1 | 0.1 | 31 |
| Example 11A | 1.4 | 1.0 | 0.22 | 4 |
| Example 12A | 1.4 | 3.7 | 0.27 | 14 |

| | Color reaction | | |
|---|---|---|---|
| | pKa ≤ 3.2 | pKa ≤ 5.0 | pKa ≥ 7.3 |
| Example 1A | − | ++ | − |
| Example 2A | − | ++ | − |
| Example 3A | + | ++ | − |
| Example 4A | + | ++ | − |
| Example 5A | − | ++ | − |
| Example 6A | + | +++ | − |
| Example 7A | + | +++ | − |

TABLE 1-continued

| | | | |
|---|---|---|---|
| Example 8A | + | +++ | − |
| Example 9A | + | +++ | − |
| Example 10A | + | +++ | − |
| Example 11A | − | + | − |
| Example 12A | + | +++ | − |

Note:
Color reaction (−: Non-occurred; +: Weak; ++: Occurred; +++: Strong)

TABLE 2

| | Carrier | | | |
|---|---|---|---|---|
| | Specific surface area: SA ($m^2/g$) | Si content (calculated as $SiO_2$) (wt %) | Na content (calculated as $Na_2O$) (wt %) | $SiO_2/Na_2O$ (weight ratio) |
| Comparative Example 1A | 1.4 | 6.1 | 0.09 | 68 |
| Comparative Example 2A | 1.4 | 0.2 | 0.36 | 0.6 |
| Comparative Example 3A | 1.1 | 0.1 | 0.12 | 0.5 |
| Comparative Example 4A | 1.4 | 3.7 | 0.27 | 14 |
| Comparative Example 5A | 1.4 | 2.8 | 0.25 | 11 |
| Comparative Example 6A | 1.4 | 0.2 | 0.36 | 11 |
| Comparative Example 7A | 1.4 | 0.2 | 0.36 | 0.6 |
| Comparative Example 8A | 1.4 | 6.1 | 0.09 | 0.6 |
| Comparative Example 9A | 1.4 | 6.1 | 0.09 | 68 |
| Comparative Example 10A | 1.4 | 6.1 | 0.09 | 68 |
| Comparative Example 11A | 1.4 | 6.1 | 0.09 | 68 |

| | Color reaction | | |
|---|---|---|---|
| | pKa ≤ 3.2 | pKa ≤ 5.0 | pKa ≥ 7.3 |
| Comparative Example 1A | ++ | +++ | − |
| Comparative Example 2A | − | − | − |
| Comparative Example 3A | − | + | − |
| Comparative Example 4A | + | +++ | − |
| Comparative Example 5A | + | +++ | − |
| Comparative Example 6A | − | − | − |
| Comparative Example 7A | − | − | − |
| Comparative Example 8A | ++ | +++ | − |
| Comparative Example 9A | ++ | +++ | − |
| Comparative Example 10A | ++ | +++ | − |
| Comparative Example 11A | ++ | +++ | − |

Note:
Color reaction (−: Non-occurred; +: Weak; ++: Occurred; +++: Strong)

TABLE 3

| | Catalyst components (concentration: on the basis of carrier) | | | | | |
|---|---|---|---|---|---|---|
| | Li (ppm) | | | Cs (ppm) | | |
| | Pre-treatment | Post-treatment | Total | Pre-treatment | Post-treatment | Total |
| Example 1A | 500 | 0 | 500 | 230 | 750 | 980 |
| Example 2A | 500 | 0 | 500 | 230 | 750 | 980 |
| Example 3A | 500 | 0 | 500 | 230 | 750 | 980 |
| Example 4A | 500 | 0 | 500 | 340 | 750 | 1090 |
| Example 5A | 500 | 0 | 500 | 340 | 750 | 1090 |
| Example 6A | 500 | 0 | 500 | 340 | 750 | 1090 |
| Example 7A | 500 | 0 | 500 | 340 | 910 | 1250 |
| Example 8A | 500 | 0 | 500 | 340 | 750 | 1090 |
| Example 9A | 500 | 0 | 500 | 340 | 750 | 1090 |
| Example 10A | 500 | 0 | 500 | 340 | 750 | 1090 |
| Example 11A | 500 | 0 | 500 | 340 | 750 | 1090 |
| Example 12A | 500 | 0 | 500 | 340 | 600 | 940 |

| | Catalyst components (concentration: on the basis of carrier) | | | | |
|---|---|---|---|---|---|
| | Re (ppm) | Re/SA (ppm)/($m^2/g$) | Cs*/Re (molar ratio) | Whole Li/Re (molar ratio) | Whole Li/Ag (weight ratio) |
| Example 1A | 420 | 420 | 2.5 | 32 | 0.0037 |
| Example 2A | 420 | 420 | 2.5 | 32 | 0.0037 |
| Example 3A | 420 | 420 | 2.5 | 32 | 0.0037 |
| Example 4A | 420 | 300 | 2.5 | 32 | 0.0037 |
| Example 5A | 420 | 300 | 2.5 | 32 | 0.0037 |
| Example 6A | 420 | 300 | 2.5 | 32 | 0.0037 |
| Example 7A | 320 | 230 | 4.0 | 42 | 0.0037 |
| Example 8A | 420 | 300 | 2.5 | 32 | 0.0037 |
| Example 9A | 520 | 370 | 2.0 | 26 | 0.0037 |
| Example 10A | 420 | 300 | 2.5 | 32 | 0.0037 |
| Example 11A | 420 | 300 | 2.5 | 32 | 0.0037 |
| Example 12A | 420 | 300 | 2.0 | 32 | 0.0037 |

| | Catalyst performance | | |
|---|---|---|---|
| | Maximum selectivity (%) | Reaction temperature (° C.) | Deterioration rate |
| Example 1A | 86.5 | 249 | 29 |
| Example 2A | 86.1 | 256 | 24 |
| Example 3A | 86.1 | 259 | 34 |
| Example 4A | 86.1 | 251 | 24 |
| Example 5A | 85.9 | 249 | 21 |
| Example 6A | 85.9 | 249 | 24 |
| Example 7A | 85.8 | 251 | — |
| Example 8A | 85.7 | 253 | 11 |
| Example 9A | 85.5 | 251 | — |
| Example 10A | 85.5 | 249 | 20 |
| Example 11A | 85.4 | 256 | 16 |
| Example 12A | 84.7 | 249 | — |

TABLE 4

| | Catalyst components (concentration: on the basis of carrier) | | | | | |
|---|---|---|---|---|---|---|
| | Li (ppm) | | | Cs (ppm) | | |
| | Pre-treatment | Post-treatment | Total | Pre-treatment | Post-treatment | Total |
| Comparative Example 1A | 500 | 0 | 500 | 340 | 750 | 1090 |
| Comparative Example 2A | 500 | 0 | 500 | 340 | 750 | 1090 |
| Comparative Example 3A | 500 | 0 | 500 | 230 | 750 | 980 |
| Comparative Example 4A | 500 | 0 | 500 | 340 | 750 | 1090 |
| Comparative Example 5A | 500 | 0 | 500 | 340 | 450 | 790 |
| Comparative Example 6A | 500 | 0 | 500 | 340 | 750 | 1090 |
| Comparative Example 7A | 500 | 0 | 500 | 340 | 450 | 790 |
| Comparative Example 8A | 500 | 0 | 500 | 340 | 750 | 1090 |
| Comparative Example 9A | 500 | 0 | 500 | 340 | 450 | 790 |
| Comparative Example 10A | 500 | 0 | 500 | 340 | 750 | 1090 |
| Comparative Example 11A | 500 | 0 | 500 | 340 | 910 | 1250 |

| | Catalyst components (concentration: on the basis of carrier) | | | | |
|---|---|---|---|---|---|
| | Re (ppm) | Re/SA (ppm)/(m$^2$/g) | Cs*/Re (molar ratio) | Whole Li/Re (molar ratio) | Whole Li/Ag (weight ratio) |
| Comparative Example 1A | 420 | 300 | 2.5 | 32 | 0.0037 |
| Comparative Example 2A | 420 | 300 | 2.5 | 32 | 0.0037 |
| Comparative Example 3A | 420 | 380 | 2.5 | 32 | 0.0037 |
| Comparative Example 4A | 210 | 150 | 5.0 | 64 | 0.0037 |
| Comparative Example 5A | 0 | 0 | — | — | 0.0037 |
| Comparative Example 6A | 0 | 0 | — | — | 0.0037 |
| Comparative Example 7A | 0 | 0 | — | — | 0.0037 |
| Comparative Example 8A | 0 | 0 | — | — | 0.0037 |
| Comparative Example 9A | 0 | 0 | — | — | 0.0037 |
| Comparative Example 10A | 0 | 0 | — | — | 0.0037 |
| Comparative Example 11A | 0 | 0 | — | — | 0.0037 |

| | Catalyst performance | | |
|---|---|---|---|
| | Maximum selectivity (%) | Reaction temperature (° C.) | Deterioration rate |
| Comparative Example 1A | 83.4 | 251 | 20 |
| Comparative Example 2A | 80.8 | 237-251 | — |
| Comparative Example 3A | 81.5 | 265 | — |
| Comparative Example 4A | 81.9 | 234 | — |
| Comparative Example 5A | 81.6 | 217 | — |
| Comparative Example 6A | 81.9 | 224 | — |
| Comparative Example 7A | 80.8 | 227 | — |
| Comparative Example 8A | 79.8 | 239 | — |
| Comparative Example 9A | 81.3 | 217 | — |
| Comparative Example 10A | 81.6 | 224 | — |
| Comparative Example 11A | 81.3 | 232 | 23 |

From the above Tables 1 to 4, there were recognized the followings.

(1) The catalysts of Examples 1A to 12A composed of Ag, Cs, Re and the carrier which were capable of satisfying a weight ratio of $SiO_2$ to $Na_2O$ ($SiO_2/Na_2O$) in the carrier of 2 to 50 (or acid sites having a pKa value of not more than 5.0), a Re content of 170 to 600 ppm per 1 m$^2$/g of a specific surface area of the carrier on the basis of a weight of the carrier, and a molar ratio of Cs* to Re (Cs*/Re) of 0.3 to 19, exhibited a maximum selectivity to ethylene oxide of 84.7 to 86.5%.

(2) In particular, the catalysts of Examples 1A to 8A using the carrier which were capable of satisfying a weight ratio of $SiO_2$ to $Na_2O$ ($SiO_2/Na_2O$) in the carrier of 6 to 27 and a molar ratio of Cs* to Re (Cs*/Re) of 2.2 to 4.5, exhibited a more preferred maximum selectivity range of 85.7 to 86.5%. Namely, it can be understood that the maximum selectivity range of these catalysts was highest in the range as described in the above (1).

(3) In the catalysts of Comparative Examples 1A to 3A using the carrier whose weight ratio of $SiO_2$ to $Na_2O$ ($SiO_2/Na_2O$) was out of the range of 2 to 50 as defined in the present invention, the maximum selectivity thereof was as low as 80.8 to 83.4%. From these results, it can be understood that in order to enhance a selectivity of the catalyst, the carrier is required to exhibit a weight ratio of $SiO_2$ to $Na_2O$ ($SiO_2/Na_2O$) which lies within the above range as defined in the present invention. Meanwhile, the difference in selectivity to ethylene oxide between the case where the weight ratio of $SiO_2$ to $Na_2O$ ($SiO_2/Na_2O$) of the carrier used fell within the above range of 2 to 50 and the case where the weight ratio was out of the specific range, was very large, i.e., 3.1% when the maximum selectivity values of both the cases were compared with each other.

(4) The catalyst of Comparative Example 4A in which the Re content per 1 m$^2$/g of a specific surface area of the carrier on the basis of a weight of the carrier was out of the range of 170 to 600 ppm as defined in the present invention exhibited a maximum selectivity as low as 81.9% as compared to those of Examples 1A to 12A. From these results, it can be understood that in order to enhance a selectivity of the catalyst, the Re content are required to lie within the respective specific ranges as defined in the present invention.

(5) In Comparative Examples 5A to 11A concerning the catalysts containing no Re, it was recognized that the weight ratio of $SiO_2$ to $Na_2O$ ($SiO_2/Na_2O$) of the carrier used had substantially no effect on selectivity of the catalyst. More specifically, in Comparative Examples 5A and 6A in which the weight ratio of $SiO_2$ to $Na_2O$ ($SiO_2/Na_2O$) of the carrier used fell within the range of 2 to 50, i.e., 11, the maximum selectivity of the catalysts was merely 81.9% as a result of optimizing the Cs content. On the other hand, in Comparative Examples 7A and 8A in which the weight ratio of $SiO_2$ to $Na_2O$ ($SiO_2/Na_2O$) of the carrier used was 0.6, the maximum selectivity of the catalysts was also as low as 80.8% even upon optimizing the Cs content. Also, in Comparative Examples 9A to 11A in which the weight ratio of $SiO_2$ to $Na_2O$ ($SiO_2/Na_2O$) of the carrier used was 68, the maximum selectivity of the catalysts was as low as 81.6% as a result of optimizing the Cs content. Thus, when the weight ratio of $SiO_2$ to $Na_2O$ ($SiO_2/Na_2O$) of the carrier used was out of the range of 2 to 50 as defined in the present invention, the maximum selectivity of the catalyst containing no Re was as low as 80.8 to 81.6% even upon optimizing the Cs content. Namely, the difference in selectivity of the catalyst containing no Re between the case where the weight ratio of $SiO_2$ to $Na_2O$ ($SiO_2/Na_2O$) of the carrier used fell within the range of 2 to 50 as defined in the present invention and the case where the weight ratio was out of the specific range, was 0.3% when the maximum selectivity values of both the cases were compared with each other. The difference value was very small, i.e., less than 1/10 time the same value of the catalyst containing Re. As a result, it can be understood that the weight ratio of $SiO_2$ to $Na_2O$ ($SiO_2/Na_2O$) of the carrier used had substantially no effect on the selectivity of the catalyst containing no Re.

Example 1B (1) Pretreatment of Carrier

The same procedure as defined in Example 1A was conducted except that the α-alumina carrier having a specific surface area of 1.4 $m^2/g$, a water absorption of 41.6% by weight, a $SiO_2$ content of 2.8% by weight, a $Na_2O$ content of 0.25% by weight, a weight ratio of $SiO_2$ to $Na_2O$ ($SiO_2/Na_2O$) of 11 and a ring shape of 8 mmφ×8 mm was used, and the amounts of lithium carbonate and cesium carbonate used were changed so as to adjust Li and Cs contents upon the pretreatment to those shown in Table 6, thereby producing a carrier impregnated with the Li and Cs components. As a result, it was confirmed that the resultant carrier had a Li content of 600 ppm and a Cs content of 340 ppm. Various properties of the carrier used are shown in Table 5.

(2) Preparation of Silver-Amine Complex Solution

The silver-amine complex solution was prepared in the same manner as defined in Example 1A.

(3) Production of Ag Catalyst

The Ag catalyst was produced in the same manner as defined in Example 1A. As a result, it was confirmed that the contents of Ag, Cs, Re and Li in the thus obtained catalyst were 13.9% (12.0% by weight on the basis of a weight of the catalyst), 1090 ppm, 420 ppm and 600 ppm, respectively, by weight on the basis of a weight of the carrier.

(4) Oxidation Reaction of Ethylene

The oxidation reaction of ethylene was conducted in the same manner as defined in Example 1A. The catalyst components and the catalyst performance of the catalyst are shown in Table 6. Meanwhile, the meanings of the respective items shown in Table 6 are the same as those shown in Tables 3 and 4.

Examples 2B to 6B and Comparative Examples 1B to 8B

First, the same procedure for "pretreatment of carrier" as defined in Example 1B was conducted except that the α-alumina carrier having properties as shown in Table 5 was used, and the amounts of lithium carbonate and cesium carbonate used were changed so as to adjust Li and Cs contents upon the pretreatment to those shown in Table 6, thereby obtaining a carrier having Li and Cs contents as shown in Table 6. Next, the silver-amine complex solution having the same composition as obtained in Example 1B was prepared, and then the same procedure for "production of Ag catalyst" as defined in Example 1B was conducted except that the concentrations of cesium nitrate and ammonium perrhenate were changed, thereby obtaining a catalyst having Cs and Re contents as shown in Table 6. At this time, in the case where Li was further supported on the catalyst upon the post-treatment, a predetermined amount of lithium nitrate ($LiNO_3$) was added into the silver-amine complex solution containing Cs and Re, thereby obtaining a catalyst having Li content as shown in Table 6, upon the "production of Ag catalyst". Meanwhile, the Ag contents of the respective catalysts produced all were 13.6% by weight on the basis of a weight of the carrier. Next, using the thus produced catalysts, the oxidation reaction of ethylene was conducted in the same manner as defined in Example 1B. The catalyst components and the catalyst performance of each catalyst are shown in Table 6.

Example 7B

First, the same procedure for "pretreatment of carrier" as defined in Example 1B was conducted except that the α-alumina carrier having properties as shown in Table 5 (water absorption: 34.6% by weight) was used, and the amounts of lithium carbonate and cesium carbonate used were changed so as to adjust Li and Cs contents upon the pretreatment to those shown in Table 6, thereby obtaining a carrier having Li and Cs contents as shown in Table 6. Next, the silver-amine complex solution having the same composition as obtained in Example 1B was prepared, and then the procedure for supporting Ag on the carrier was conducted by the following two divided operations.

(First Operation of the Ag-Supporting Procedure)

1.3 mL of water was added to 12.7 g of the above-prepared silver-amine complex solution to obtain an impregnating solution. The thus obtained impregnating solution was impregnated in 30 g of the α-alumina carrier impregnated with Li and Cs in an evaporator under reduced pressure while heating at 40° C. The thus impregnated carrier was heated by superheated steam at 200° C. for 15 min while flowing the steam at a rate of 2 m/sec.

(Second Operation of the Ag-Supporting Procedure)

12.7 g of the above-prepared silver-amine complex solution was mixed with 0.5 mL of an aqueous solution containing 9.97% by weight of cesium nitrate ($CsNO_3$), 0.5 mL of an aqueous solution containing 5.75% by weight of ammonium perrhenate ($NH_4ReO_4$), 0.2 mL of an aqueous solution containing 10.1% by weight of lithium nitrate ($LiNO_3$) and 0.2 mL of water to prepare an impregnating solution. The thus prepared impregnating solution was impregnated in the carrier obtained after completing the first operation of the Ag-supporting procedure in an evaporator under reduced pressure while heating at 40° C. The thus obtained impregnated carrier was heated by superheated steam at 200° C. for 15 min while flowing the steam at a rate of 2 m/sec, thereby producing a catalyst. As a result, it was confirmed that the contents of Ag, Cs, Re and Li in the catalyst were 26.2% by weight (20.8% by weight on the basis of a weight of the catalyst), 1500 ppm, 530 ppm and 660 ppm, respectively, on the basis of a weight of the carrier. Next, using the thus produced catalyst, the oxidation reaction of ethylene was conducted in the same manner as defined in Example 1B. The catalyst components and the catalyst performance of the catalyst are shown in Table 6.

TABLE 5

| | Carrier | | | |
|---|---|---|---|---|
| | Specific surface area: SA ($m^2/g$) | Si content (calculated as $SiO_2$) (wt %) | Na content (calculated as $Na_2O$) (wt %) | $SiO_2/Na_2O$ (weight ratio) |
| Example 1B | 1.4 | 2.8 | 0.25 | 11 |
| Example 2B | 1.4 | 2.8 | 0.25 | 11 |
| Example 3B | 1.4 | 2.8 | 0.25 | 11 |
| Example 4B | 1.4 | 2.8 | 0.25 | 11 |
| Example 5B | 1.4 | 2.8 | 0.25 | 11 |
| Example 6B | 1.0 | 3.1 | 0.26 | 12 |
| Example 7B | 1.4 | 3.7 | 0.27 | 14 |
| Comparative Example 1B | 1.4 | 2.8 | 0.25 | 11 |
| Comparative Example 2B | 1.4 | 2.8 | 0.25 | 11 |
| Comparative Example 3B | 1.4 | 2.8 | 0.25 | 11 |
| Comparative Example 4B | 1.4 | 2.8 | 0.25 | 11 |
| Comparative Example 5B | 1.4 | 2.8 | 0.25 | 11 |
| Comparative Example 6B | 1.4 | 2.8 | 0.25 | 11 |
| Comparative Example 7B | 1.0 | 3.1 | 0.26 | 12 |
| Comparative Example 8A | 1.0 | 3.1 | 0.26 | 12 |

TABLE 6

| | Catalyst components (concentration: on the basis of carrier) | | | | | |
|---|---|---|---|---|---|---|
| | Li (ppm) | | | Cs (ppm) | | |
| | Pre-treatment | Post-treatment | Total | Pre-treatment | Post-treatment | Total |
| Example 1B | 600 | 0 | 600 | 340 | 750 | 1090 |
| Example 2B | 500 | 60 | 560 | 340 | 750 | 1090 |
| Example 3B | 500 | 170 | 670 | 340 | 750 | 1090 |
| Example 4B | 500 | 230 | 730 | 340 | 750 | 1090 |
| Example 5B | 500 | 0 | 500 | 340 | 750 | 1090 |
| Example 6B | 500 | 0 | 500 | 230 | 750 | 980 |
| Example 7B** | 570 | 90 | 660 | 350 | 1150 | 1500 |
| Comparative Example 1B | 0 | 60 | 60 | 340 | 750 | 1090 |
| Comparative Example 2B | 0 | 170 | 170 | 340 | 750 | 1090 |
| Comparative Example 3B | 500 | 0 | 500 | 340 | 450 | 790 |
| Comparative Example 4B | 500 | 0 | 500 | 340 | 750 | 1090 |
| Comparative Example 5B | 600 | 0 | 600 | 340 | 450 | 790 |
| Comparative Example 6B | 600 | 0 | 600 | 340 | 750 | 1090 |
| Comparative Example 7B | 500 | 0 | 500 | 230 | 450 | 680 |
| Comparative Example 8A | 600 | 0 | 600 | 230 | 450 | 680 |

TABLE 6-continued

| | Catalyst components (concentration: on the basis of carrier) | | | | |
|---|---|---|---|---|---|
| | Re (ppm) | Re/SA (ppm)/($m^2/g$) | Cs*/Re (molar ratio) | Whole Li/Re (molar ratio) | Whole Li/Ag (weight ratio) |
| Example 1B | 420 | 300 | 2.5 | 38 | 0.0044 |
| Example 2B | 420 | 300 | 2.5 | 36 | 0.0041 |
| Example 3B | 420 | 300 | 2.5 | 43 | 0.0049 |
| Example 4B | 420 | 300 | 2.5 | 47 | 0.0054 |
| Example 5B | 420 | 300 | 2.5 | 32 | 0.0037 |
| Example 6B | 420 | 420 | 2.5 | 32 | 0.0037 |
| Example 7B* | 530 | 380 | 3.0 | 33 | 0.0025 |
| Comparative Example 1B | 420 | 300 | 2.5 | 4 | 0.0004 |
| Comparative Example 2B | 420 | 300 | 2.5 | 11 | 0.0012 |
| Comparative Example 3B | 0 | — | — | — | 0.0037 |
| Comparative Example 4B | 0 | — | — | — | 0.0037 |
| Comparative Example 5B | 0 | — | — | — | 0.0044 |
| Comparative Example 6B | 0 | — | — | — | 0.0044 |
| Comparative Example 7B | 0 | — | — | — | 0.0037 |
| Comparative Example 8A | 0 | — | — | — | 0.0044 |

| | Catalyst performance | | |
|---|---|---|---|
| | Maximum selectivity (%) | Reaction temperature (° C.) | Deterioration rate |
| Example 1B | 86.2 | 244 | 4.8 |
| Example 2B | 85.3 | 250 | 8.7 |
| Example 3B | 85.4 | 243 | 9.1 |
| Example 4B | 86.0 | 248 | 8.5 |
| Example 5B | 85.5 | 247 | 11.0 |
| Example 6B | 86.1 | 256 | 24.0 |
| Example 7B** | 86.3 | 228 | 2.5 |
| Comparative Example 1B | 84.0 | 256 | 33.0 |
| Comparative Example 2B | 83.4 | 257 | 80.0 |
| Comparative Example 3B | 81.4 | 219 | 4.0 |
| Comparative Example 4B | 81.7 | 228 | — |
| Comparative Example 5B | 81.3 | 217 | — |
| Comparative Example 6B | 81.5 | 227 | — |
| Comparative Example 7B | 81.6 | 229 | — |
| Comparative Example 8A | 81.6 | 228 | — |

Note
**Ag content on the basis of catalyst: 20.8% by weight

From the results shown in Tables 5 and 6, there were recognized the followings.

(1) The catalysts of Examples 1B to 6B which were composed of Ag, Li, Cs, Re and the carrier and had a total Li content within a range of 400 to 1000 ppm on the basis of a weight of the carrier exhibited a maximum selectivity of to 86.2% and a deterioration rate of 4.8 to 24.0, whereas the catalysts of Comparative Examples 1B and 2B whose Li content was out of the above specific range exhibited a maximum selectivity of 83.4 to 84.0% and a deterioration rate of 33.0 to 80.0. That is, in Comparative Examples 1B and 2B, the selectivity was lowered by 2.1% and the deterioration rate was increased by 6.9 times as compared to those of Examples 1B to 6B. Thus, it can be understood that when the Li content lies within the above specific range, the catalyst life is stabilized.

(2) In particular, the catalysts of 1B to 4B having a total Li content within a range of 550 to 1000 ppm on the basis of a weight of the carrier exhibited a maximum selectivity as high as 85.3 to 86.2% and a deterioration rate as low as 4.8 to 9.1, whereas the catalysts of Examples 5B and 6B whose Li content was out of the above specific range exhibited a maximum selectivity of 85.5 to 86.1% and a deterioration rate of 11.0 to 24.0. That is, the deterioration rate of the catalysts of Examples 5B and 6B was 2.3 times that of the catalysts of Examples 1B to 4B. Thus, it can be understood that when the Li content lies within the above specific range, the catalyst life is further stabilized.

(3) Also, in Examples 1B to 5B and Comparative Examples 3B to 6B, or in Example 6B and Comparative Examples 7B and 8B, as shown in Table 5, the same carriers were respectively used, and the total Li content therein all fell within the range of 400 to 1000 ppm. Therefore, the difference between Examples 1B to 5B and Comparative Examples 3B to 6B or between Example 6B and Comparative Examples 7B and 8B was that the catalysts of the Comparative Examples contained no Re. The selectivity values of Examples 1B to 5B were in the range of 85.3 to 86.2%, and the selectivity values of Comparative Examples 3B to 6B were in the range of 81.3 to 81.7%. Whereas, the selectivity values of Example 6B was 86.1%, and the selectivity values of Comparative Examples 7B and 8B both were 81.6%. Thus, it can be understood that the catalysts containing Re exhibited a higher selectivity than those containing no Re. That is, it can be understood that in the case where the carrier used in the catalyst had a specific surface area of 0.6 to 3.0 m$^2$/g, and the Li content therein fell within the range of 400 to 1000 ppm on the basis of a weight of the carrier, the addition of Re to the catalyst was effective to enhance the selectivity thereof.

(4) In Example 7B in which the Ag-supporting procedure was conducted by two divided operations to enhance the Ag-supporting rate, the deterioration rate of the catalyst was 2.5 which showed that the catalyst life was considerably improved.

What is claimed is:

1. A catalyst for producing ethylene oxide from ethylene, comprising at least silver (Ag), lithium (Li), cesium (Cs), rhenium (Re) and a carrier, said catalyst is produced by optionally pretreating the carrier to support an alkali metal thereon in which the carrier has a specific surface area of 0.6 to 3.0 m$^2$/g and a weight ratio of a silicon (Si) content to a sodium (Na) content of 6 to 27 in terms of SiO$_2$/Na$_2$O; a content of Re in the catalyst is 170 to 600 ppm per 1 m$^2$/g of the specific surface area of the carrier on the basis of a weight of the carrier; a molar ratio of Cs to Re (Cs/Re) in the catalyst is 2.2 to 4.5; a molar ratio of Li to Re (Li/Re) in the catalyst is 25 to 63 and the content of Li is 400 to 1000 ppm on the basis of a weight of the carrier.

2. A catalyst according to claim 1, wherein the Si content in the carrier is 0.5 to 7.0% by weight in terms of SiO$_2$.

3. A catalyst according to claim 1, wherein the Na content in the carrier is 0.05 to 0.50% by weight in terms of Na$_2$O.

4. A catalyst according to claim 1, wherein lithium (Li) is supported on the carrier as a pretreatment material and a Li content in the pretreated carrier is 100 to 1000 ppm.

5. A catalyst according to claim 1, cesium (Cs) is supported on the carrier as a pretreatment material and a Cs content in the pretreated carrier is 100 to 1000 ppm.

6. A catalyst according to claim 1, wherein a content of silver in the catalyst is 5 to 40% by weight on the basis of a whole weight of the catalyst.

* * * * *